United States Patent [19]
Johnson et al.

[11] Patent Number: 4,784,640
[45] Date of Patent: Nov. 15, 1988

[54] APPARATUS FOR IMPLANTING IMPLANTS IN CATTLE

[76] Inventors: Ronald F. Johnson, 3652 Brocker; Norman E. Nicklas, 5120 Hurd, both of, Metamora, Mich. 48455

[21] Appl. No.: 895,804

[22] Filed: Aug. 12, 1986

Related U.S. Application Data

[63] Continuation of Ser. No. 642,525, Aug. 20, 1984, Pat. No. 4,659,326.

[51] Int. Cl.4 ............................................. A61M 5/18
[52] U.S. Cl. ...................................... 604/62; 604/64; 206/490
[58] Field of Search ................... 604/59–64, 604/891; 128/1 R; 206/438, 439, 347, 490, 486, 562, 563

[56] References Cited

U.S. PATENT DOCUMENTS

| 2,784,405 | 3/1957 | Working | 206/347 X |
| 3,858,571 | 1/1975 | Rudolph | 128/1 R |
| 3,951,132 | 4/1976 | Bucalo | 128/1 R |
| 4,252,110 | 3/1981 | Behney | 128/1 R |
| 4,444,310 | 4/1984 | Odell | 206/438 X |
| 4,451,254 | 5/1984 | Dinius et al. | 604/62 |
| 4,506,680 | 3/1985 | Stokes | 128/786 |

*Primary Examiner*—Michael H. Thaler
*Attorney, Agent, or Firm*—Harness, Dickey & Pierce

[57] ABSTRACT

A retainer for cattle implants comprising a main body portion and a plurality of retention elements capable of implantation into cattle along with the implant itself. An injector and new process of implanting is also disclosed wherein a double acting trigger mechanism on an injector properly loads a retainer and implant into a needle and then injects the retainer and implant into the animal.

1 Claim, 3 Drawing Sheets

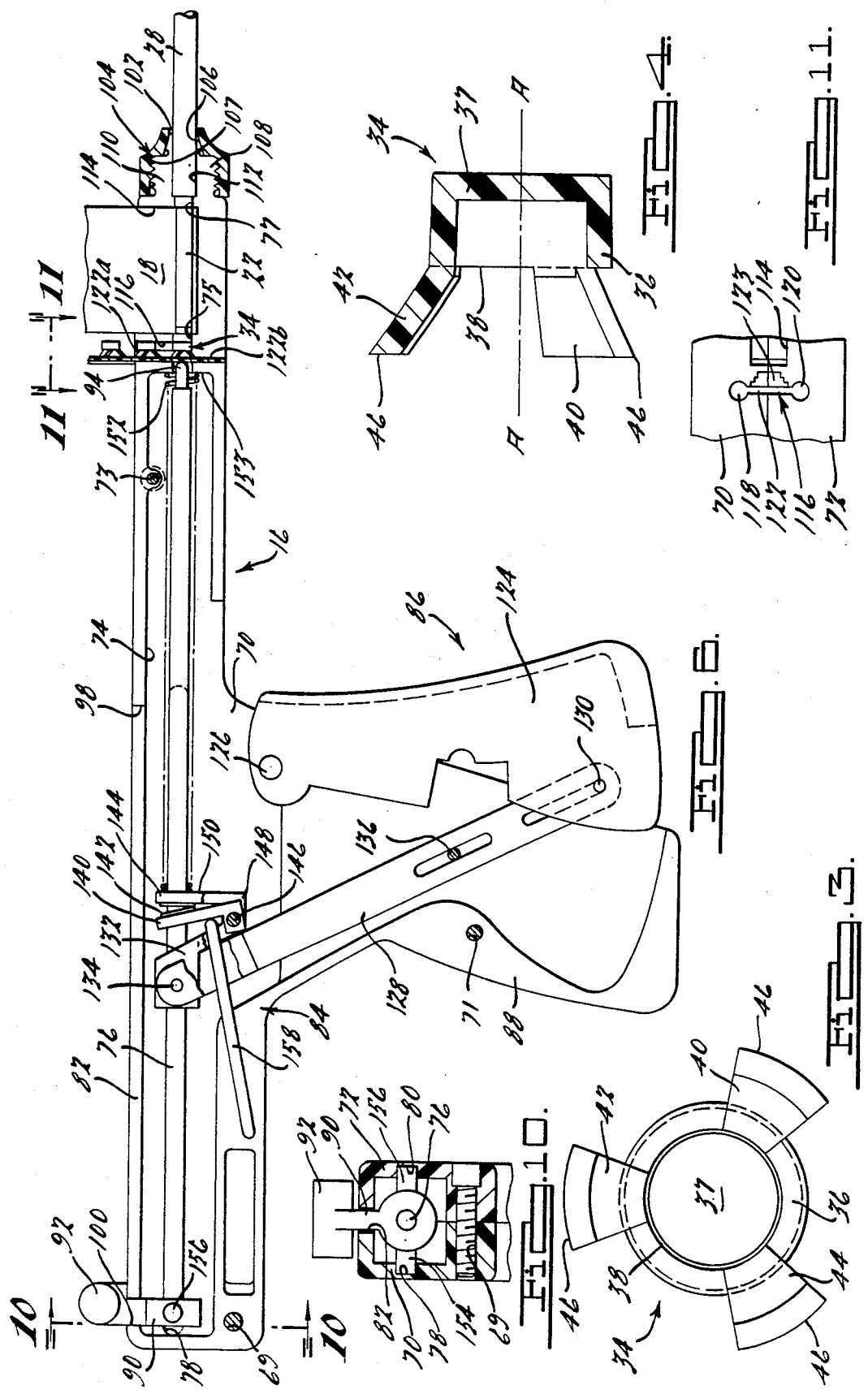

APPARATUS FOR IMPLANTING IMPLANTS IN CATTLE

This is a continuation of U.S. patent application Ser. No. 642,525 filed Aug. 20, 1984 now U.S. Pat. No. 4,659,326.

BACKGROUND AND SUMMARY OF THE INVENTION

The present invention relates generally to implanting cattle and in particular relates to implanting of drugs into feed animals to increase the size of the animal prior to slaughter.

Cattle farmers uniformly implant cattle with growth hormones or steroids due to the higher feed efficiency, added weight gains, and lower cost per animal than a feed mix or other method. The implants are approved by the United States Food and Drug Administration (USFDA) and must be implanted, under such approval, in a specific location in the back of the ear of the animal between the hide and the first layer of tissue. The placement of the implant in the proper location permits the proper time release of the steriod or growth hormone into the animal. The cost of the implants is over $2.00 per head of cattle over an eight to nine month period over which period each head of cattle will gain an extra thirty to fifty pounds.

The process generally involves confining the animal to be implanted in a squeeze chute, loading the implant in an injector, grasping the tip of the animal's ear in one hand and the injector in the other, penetrating under the skin with the needle of the injector on the back side of the middle third of the animal's ear, fully inserting the needle between the skin and cartilage while avoiding major blood vessels, pulling the needle back (to remove the needle) as the plunger of the injector is pushed forward to place the implant in the ear of the animal. Optional hygiene techniques may also add steps at various points in the process.

To protect against infection due to the breakage of the skin or hide, some implants have an antibiotic coating, such as that used in COMPUDOSE, an estradiol sold by the Elanco Division of Eli Lilly & Co., approved for steers and calves and having a 200 day period of usefulness. The antibiotic coating, however, has a silicone base which causes a significant percentage of the implants to be expelled by the animal from its ear prior to the healing of the hide at the insertion point. Expulsion of the implant not only costs the farmer the expense of the implant, but also causes the farmer to lose the income he would have acquired from the thirty to fifty pounds of meat that each head of cattle would have acquired if the implant had remained in place the entire period of desired implantation. Other implants having a shorter term of usefulness than COMPUDOSE are sold under the trade names RALGRO (by International Minerals & Chemical Corporation, Terre Haute, Ind.) and SYNOVEX (by Syntex Corp.).

The present invention seeks to improve the implantation technique and the retention level of the implants in the animals. A retainer has been developed by applicants which can be inserted along with the implant to retain the antibiotic coated implant in the ear with great success. The retainer has the object of improving its effectiveness in direct proportion to the conditions that had decreased the effectiveness of the implant without the retainer, particularly becoming increasingly effective as the implant moves in a direction towards the hole caused by the injector needle during implantation.

Further, a packaged set of the retainers has been developed, which is insertable into an injector also developed by applicants, to conveniently implant the drug and the retainer into the ears of cattle in a large scale operation. Packaging of the implants and retainers in the same cartridge is also within the scope of the invention.

The injector of the present invention has the additional advantages of a gravity feed for the retainers and implants, universatility for right-handed or left-handed use of the injector by the operator, and the convenience of a requirement that only one hand need be used to operate the injector during the implantation process.

The method of implanting is also improved by the implantation of the retainer and implant together, particularly when used in connection with the injector of the present invention.

Other objects, features and advantages of the present invention will become apparent from the following detailed description taken in conjunction with the accompanying drawings.

BRIEF DESCRIPTION OF THE DRAWINGS

FIG. 4 is a side sectional view of the retainer;

FIG. 5 is an elevated view of a package of retainers as insertable into the injector;

FIG. 6 is a vertical side sectional view of the injector of FIG. 1;

FIG. 10 is a vertical rear sectional view of the injector; and

FIG. 11 is a top elevated view of the load slots of the injector.

DETAILED DESCRIPTION OF THE PREFERRED EMBODIMENTS

Figure 1:
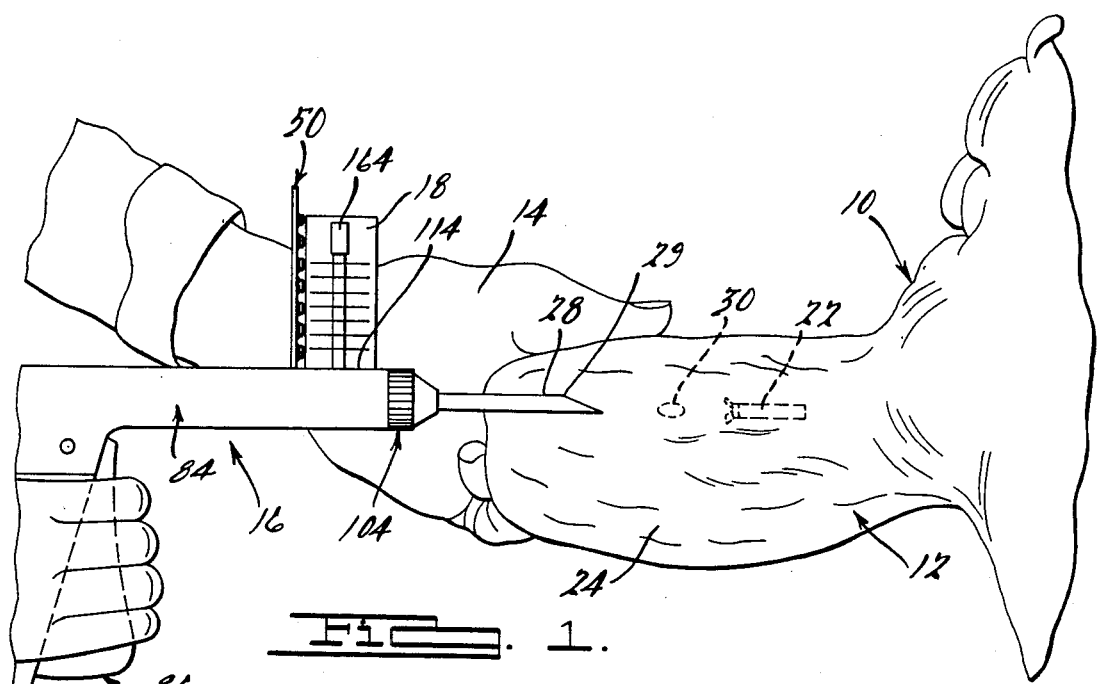
FIG. 1 is an elevated view illustrating the injector just prior to placement in the ear of the animal.

Referring to FIG. 1, an animal 10 is shown with its ear 12 being held in the left hand 14 of the operator of an injector 16. The animal's head is held in place by a conventional yoke mechanism. The injector 16 has an unmodified cartridge 18 of COMPUDOSE implants inserted therein, with the protective cap (not shown) of the COMPUDOSE cartridge removed. The injector 16 is held in the operator's right hand 20, but is actually universal to either right or left handed use.

Figure 2:
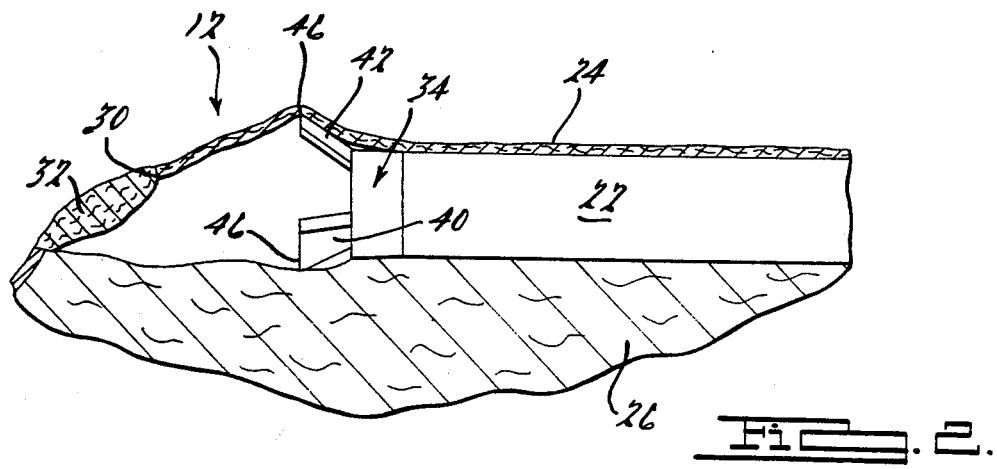
FIG. 2 is an enlarged vertical side sectional view of the implant retained in the animal's ear by the retainer.

As illustrated in FIGS. 1 and 2, the goal of implantation is to place an implant 22 in a specific location in the animal's ear 12 between the hide 24 and the tissue 26 of the ear 12 and have it be retained there for the period of usefulness of the implant 22. With COMPUDOSE, that period is 200 days. The approved location behind the ear 12 has a very low number of blood vessels per square inch relative to other parts of the animal 10 and permits the best controlled time release of the steroid or growth hormone by the animal 10 into its system over the longest period of time.

As can be seen in FIG. 1, the needle 28 used for insertion of the implant is approximately ⅜ of an inch interior dimension and approximately three inches long.

The needle may include a nib 29 to keep a loaded implant from releasing from the needle 28 prior to the desired time. The hole 30 remaining when the needle 28 has been withdrawn from the animal's ear 12 is substantial. In many cases, an animal 10 can take up to a week before the hole 30 is completely closed by scar tissue 32. The implant 22 may be expelled through this hole 30 at any time by the animal 10, either by the animal rubbing its ear against another object, or merely by the implant 22 being shaken loose by the animal through the hole 30 in its hide 24.

Figure 3:
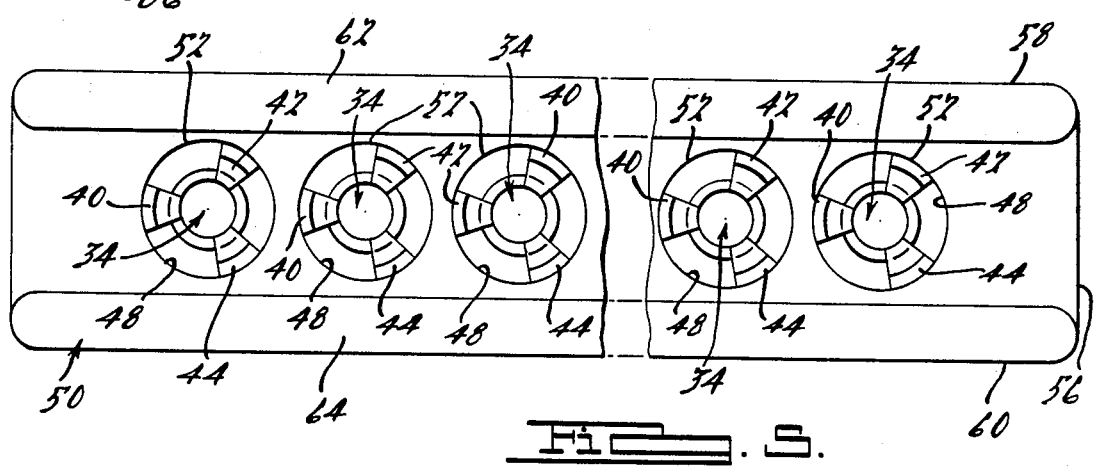
FIG. 3 is an elevated end view of the retainer.

The present invention includes a retainer 34 that maintains the implant 22 in place during such movement. The retainer 34 (FIGS. 2, 3, and 4) has a cylindrical hollow main body portion 36 closed at one end 37 and from the other end 38 has three retention elements 40, 42, and 44 extending from it and forming an angle with the axis A—A of the body portion 36. The retention elements 40, 42, and 44 have both radial and axial components as they are directed away from the body portion 36. The retainer 34 is made of an USFDA approved polyethylene allowed to be inserted by the USFDA into various animals, including cattle. The retention elements 40, 42, and 44 are flexible, each having a free forward edge 46 capable of planting the retention elements 40, 42, or 44 against the animal hide 24 or tissue 26 if any force is exerted against the retainer body portion 36 by the implant 22 due to any movement by the animal 10 that may force the implant 22 outward. Any force applied to the main body portion 36 of the retainer 34 by the implant 22 also flexes the retention elements 40, 42, and 44 radially outwardly as they are forced against the adjacent hide 24 or tissue 26 material against which they are planted, as shown in FIG. 2. The main body portion 36 thus acts as an abutment to hold the implant 22 in place via the retention elements 40, 42, and 44.

The retainers 34 are packaged, as shown in FIG. 5, within a series of apertures 48 in a frame 50 and integral with the frame 50 at an interface between each of the retention elements 40, 42, and 44 of the retainer 34 and the edge 52 of each respective aperture. Thus, the entire package of retainers is made in one injection mold operation. The frame also has a leading edge 54, a trailing edge 56, and a pair of parallel elongated edges 58 and 60 along with a pair of guide tracks 62 and 64 are disposed as will be discussed in greater detail below.

The injector 16 itself is shown in FIGS. 6, 7, 8, 9 and 10. The injector 16 is effectively a gun having a double acting trigger mechanism. The injector 16 comprises a two piece housing 70 and 72 (FIG. 10) within which is disposed a bore 74 within which a plunger rod 26 moves. The bore 74 narrows at the front portion of the injector 16 to form two spaced apart bores 75 and 77 which aid in guiding the movement of the plunger rod 76. The bore 74 also has a longitudinal groove 78 and 80 (FIG. 10) on each side of the bore 74, one in each housing section 70 and 72. The housing sections 70 and 72 also form a slot 82 at the top of the injector housing 84 to communicate the bore 74 with the exterior of the housing 84 via the slot 82. The housing sections 70 and 72 are secured together by suitable bolts via threaded bores 69, 71, and 73.

Figure 9:
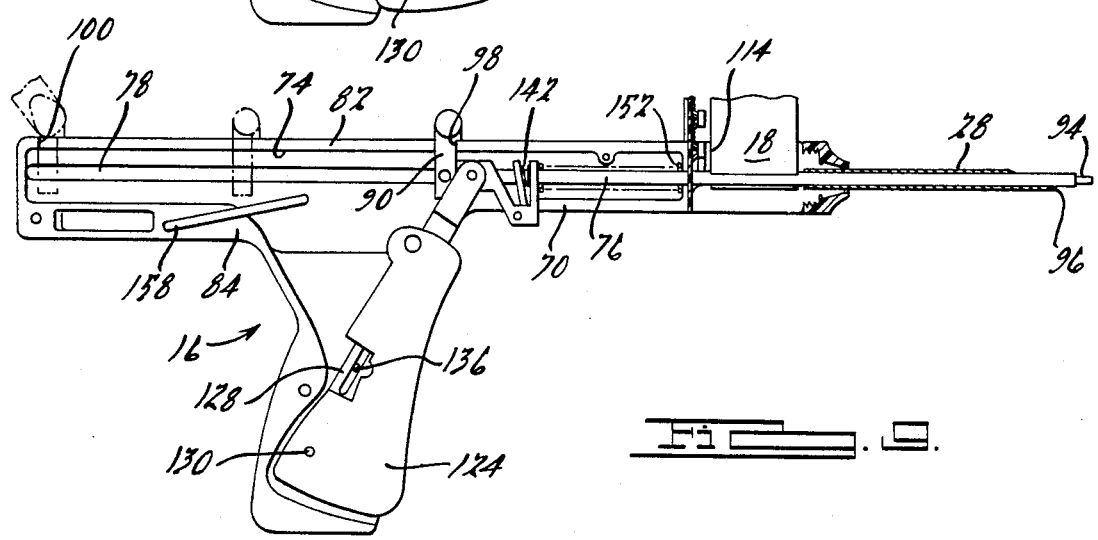

The plunger rod 76 is moved by a hand trigger 86 mounted in a centrally disposed extended portion 88 of the housing 84 between the two housing halves 70 and 72. A first post 90 connected to one end of the plunger rod 76 and slidably movable therewith extends through the upper slot 82 with a manually engageable lug 92 fixedly mounted to the post 90 outside of the housing 84. The plunger rod 76 is of a length such that the front end 94 of the plunger rod 76 can extend beyond the end tip 96 of the needle 28 at the point that the first post 90 reaches the front end 98 of the slot 82 as shown in FIG. 9. The front 98 and rear 100 ends of the slot 82 act to positively stop the first post 90 and provide the limits of travel of the plunger rod 76.

The needle 28 is associated with the injector 16 and the bore 74 at the front end 102 of the injector via a holding cap 104 which also acts to hold the front end 102 of the injector 16 and the needle 28 together. The cap 104 has a narrow central bore 106 expanding into a larger internally threaded bore 107 with mates with the external thread 108 of the housing 84 at the front extension 110 thereof. The needle 28 is inserted through the narrow bore 106 in the cap 104 into the housing 84 at a counterbore 112 located at the front end of the plunger bore 74. As the cap 104 is tightened, the housing halves 70 and 72 also clamp against the needle 28 to secure the needle 28 to the housing 84.

A slot 114 communicating the internal bore 74 (or 75 and 77) with the exterior of the housing is located just behind the cap 104 for location of the cartridge 18 of COMPUDOSE implants. A second slot 116 is disposed behind the cartridge slot 114 and comprises, as shown in FIG. 11, two elongated vertical throughbores 118 and 120 in a plane perpendicular to the axis of movement of the plunger rod 76 and a narrow connecting bore 122 between the elongated vertical bores 118 and 120 for placement of the package of retainers 50. The upper section 122a of the connecting bore has a greater width above the plunger rod bore 75 than the lower section 122b below such that a ledge or stop 123 exists to locate the next available retainer 34 from a package 50 inserted in the bore 122.

The trigger mechanism 86 comprises a hollow hand engaging member 124 which is pivoted at the upper portion thereof on a pin 126 on each side of the member 124 engageable into bores (not shown) within each of the housing sections 70 or 72. The lower portion of the hand engaging mechanism is first pivoted to a yoke element 128 at pin 130 passing only through the member 124. The yoke element 128 is in turn pivoted to a slider 132 via pins 134 on both sides of the slider 132 and also yoked at an intermediate location on a pin 136 extending between the two housing sections 70 and 72.

The slider 132 slides along the plunger rod 76. At an intermediate location in the slider 132, a block 140 through which the plunger rod 76 passes is pivoted. The block 140 is biased by a first spring 142 away from the front portion 144 of the slider 132, and pivoted via a pin 146 to the lower end 148 of the slider 132. The block 140 may be counterweighted, as shown in FIG. 6, to lessen the bias needed by the first spring 142. The front surface 150 of the slider 132 in turn acts against a second biasing spring 152 to bias the slider 132 away from the front end 153 of the slot. It should also be noted that the plunger rod 76 is stabilized within the bore 74 by lugs 154 and 156 extending laterally from the plunger rod 76 at the first post 90 into the grooves 78 and 80 in each housing section 70 and 72 at the respective side of the bore 74.

A trip element 158 is also included in the housing 84 and fixedly mounted to one of the housing sections to force the block 140 forward when the block 140 contacts the trip element 158, which action will be described in more detail below.

Figure 7:
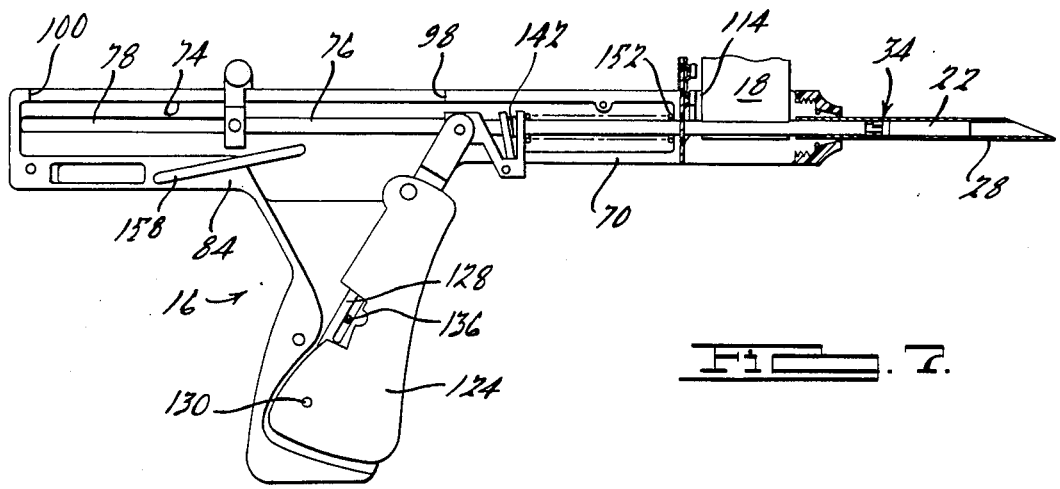
FIGS. 7, 8, and 9 are views similar to FIG. 6 illustrating the injector at various positions during the actuation of the injector.
Figure 8:
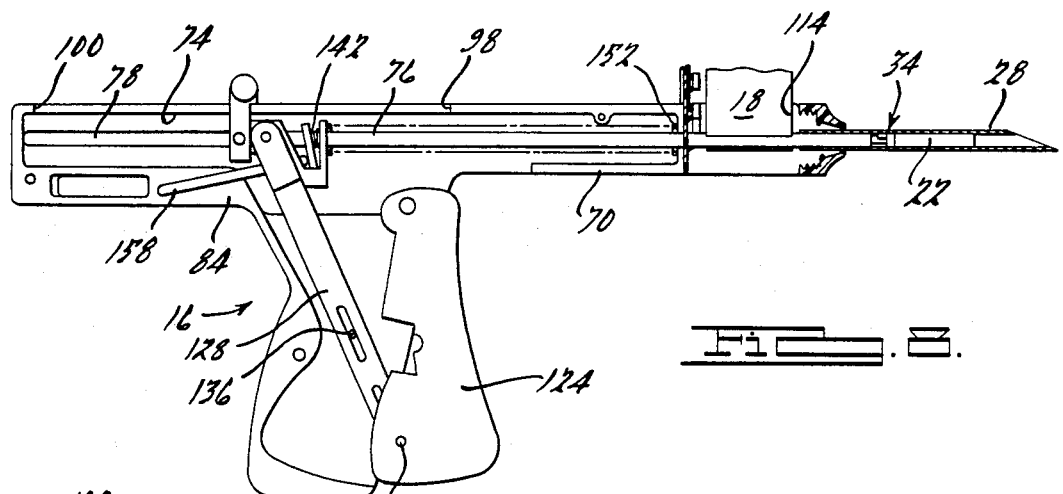

In operation, as shown in FIG. 6, the injector 16 is loaded with the cartridge 18 of COMPUDOSE and a package 50 of retainers. Referring to FIG. 7, the first action is movement of the plunger rod 76 to load the injector 16 by breaking the lowest retainer 34 free from the package 50 into association with the implant 22 and placing both the retainer 34 and the implant 22 into the needle 28 for readiness to inject into the animal. This action is performed by squeezing the trigger 86 to its limit. The loading procedure of FIG. 7 also locks the block 140 into position by friction against the plunger rod 76 (via the trip element 158) to place tension on the injector spring 152, but only permits the plunger rod 76 to travel approximately half its axial dimension (since the slider 132 can only travel that far) so that the implant 22 is not prematurely injected. At the end of this first stroke, when the hand trigger 86 is released, the block 140 is freed by the combined force of the two springs 142 and 152 to slide the slider 132 back until the block 140 again contacts the trip element 158, as shown in FIG. 8. Either just before or just after this action, the farmer will have restricted the animal's head in a squeeze chute, grabbed the animal's ear and penetrated its hide with the needle 28 in the proper location as regulated by the USFDA.

When the hand trigger 86 is then squeezed a second time, as shown in FIG. 9, the plunger rod 76 will move forward until the first post 90 is set against the front end 98 of the upper slide slot 82, driven due to the frictional interface between the block 140 and the plunger rod 76 (via the trip element 158) by movement of the hand trigger 124. At this point, the front end 94 of the plunger rod 76 will have traversed the length of the needle 28 and into the animal to implant both the retainer 34 and the implant 22 into the animal's ear. The needle 28 is withdrawn concurrently with the placement of the retainer 34 and implant 22 in the ear of the animal. The injector is then cocked for the next implantation by pulling the lug 92 to the rear end 100 of the slot 82 after the animal has been freed from the squeeze chute.

Once a retainer 34 and implant 22 have been implanted and the plunger rod 76 cocked to its initial position, as shown in FIG. 6, the package of retainers 50 will automatically slide down into the next position with the next retainer 34 itself acting as a positive stop against the housing 84 adjacent the COMPUDOSE implant at slot 122b to properly locate the packaged retainer 34 in the injector 16. The next implant 22 will either move down by gravity or be advanced by a knob 164 (FIG. 1) on the cartridge 18 to the next position, depending on the cartridge design. In the COMPUDOSE cartridge 18 shown, the next implant 22 must be manually placed into the injector by advancing the knob 164 in the cartridge 18 to the next position (FIG. 1). Neither situation will affect the performance of this injector 16, however.

While it will be apparent that the preferred embodiments of the invention disclosed are well calculated to provide the advantages and features above stated, it will be appreciated that the invention is susceptible to modification, variation and change without departing from the spirit and scope of the invention, as defined by the appended claims.

We claim:

1. A system for implantation of growth hormone implants or the like having a package adapted to be injected into animals comprising:
   a cartridge;
   a plurality of implants disposed in said cartridge;
   a plurality of retainers for retention of said implants in the animals disposed adjacent to said implants such that each retainer is aligned with a corresponding implant;
   an injector including means for receiving said cartridge and said retainers, said means enabling proper disposition of each said implant with each corresponding retainer within said injector for implantation of said implants and retainers into the animals.

* * * * *